US008298677B2

(12) United States Patent
Wiesner et al.

(10) Patent No.: US 8,298,677 B2
(45) Date of Patent: Oct. 30, 2012

(54) FLUORESCENT SILICA-BASED NANOPARTICLES

(75) Inventors: Ulrich Wiesner, Ithaca, NY (US);
Hooisweng Ow, Arlington, MA (US);
Daniel R. Larson, Long Island City, NY (US); Watt W. Webb, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 1442 days.

(21) Appl. No.: 10/536,569

(22) PCT Filed: Nov. 26, 2003

(86) PCT No.: PCT/US03/37963
§ 371 (c)(1),
(2), (4) Date: May 2, 2006

(87) PCT Pub. No.: WO2004/074504
PCT Pub. Date: Sep. 2, 2004

(65) Prior Publication Data
US 2006/0183246 A1 Aug. 17, 2006

Related U.S. Application Data

(63) Continuation of application No. 10/306,614, filed on Nov. 26, 2002, now abandoned.

(51) Int. Cl.
*B32B 19/00* (2006.01)
*B32B 17/00* (2006.01)
(52) U.S. Cl. ......... 428/428; 428/447; 977/702; 977/977
(58) Field of Classification Search .................. None
See application file for complete search history.

(56) References Cited

U.S. PATENT DOCUMENTS

| | | | |
|---|---|---|---|
| 4,279,617 A | 7/1981 | Masson et al. | |
| 4,774,339 A | 9/1988 | Haugland et al. | |
| 4,810,636 A | 3/1989 | Corey | |
| 4,812,409 A | 3/1989 | Babb et al. | |
| 5,187,288 A | 2/1993 | Kang et al. | |
| 5,248,782 A | 9/1993 | Haugland et al. | |
| 5,260,957 A | 11/1993 | Hakimi et al. | |
| 5,274,113 A | 12/1993 | Kang et al. | |
| 5,433,896 A | 7/1995 | Kang et al. | |
| 5,639,603 A | 6/1997 | Dower et al. | |
| 5,830,912 A | 11/1998 | Gee et al. | |
| 5,981,180 A | 11/1999 | Chandler et al. | |
| 5,990,479 A | 11/1999 | Weiss et al. | |
| 6,132,773 A * | 10/2000 | Amiche ......................... 424/490 |
| 6,180,415 B1 | 1/2001 | Schulz et al. | |
| 6,207,392 B1 | 3/2001 | Weiss et al. | |
| 6,251,303 B1 | 6/2001 | Bawendi et al. | |
| 6,268,222 B1 | 7/2001 | Chandler et al. | |
| 6,274,323 B1 | 8/2001 | Bruchez et al. | |
| 6,306,610 B1 | 10/2001 | Bawendi et al. | |
| 6,319,426 B1 | 11/2001 | Bawendi et al. | |
| 6,322,901 B1 | 11/2001 | Bawendi et al. | |
| 6,326,144 B1 | 12/2001 | Bawendi et al. | |
| 6,344,272 B1 | 2/2002 | Oldenburg et al. | |
| 6,423,551 B1 | 7/2002 | Weiss et al. | |
| 6,426,513 B1 | 7/2002 | Bawendi et al. | |
| 6,444,143 B2 | 9/2002 | Bawendi et al. | |
| 6,454,789 B1 | 9/2002 | Chen et al. | |
| 6,479,146 B1 | 11/2002 | Caruso et al. | |
| 6,500,622 B2 | 12/2002 | Bruchez, Jr. et al. | |
| 6,548,264 B1 | 4/2003 | Tan et al. | |
| 6,576,219 B2 | 6/2003 | Brandt et al. | |
| 6,649,138 B2 | 11/2003 | Adams et al. | |
| 2002/0048800 A1 * | 4/2002 | Gu et al. ...................... 435/183 |
| 2003/0017264 A1 | 1/2003 | Treadway et al. | |
| 2003/0124564 A1 * | 7/2003 | Trau et al. ......................... 435/6 |

FOREIGN PATENT DOCUMENTS

| | | |
|---|---|---|
| WO | WO96/10282 | 4/1996 |
| WO | WO99/50916 A | 10/1999 |
| WO | WO00/32542 * | 6/2000 |

OTHER PUBLICATIONS

Definition for "Ligand" downloaded from Merriam-Webster Online Dictionary; downloaded on Dec. 10, 2008.*
van Blaaderen et al. The Colloid Chemistry of Silica. Chapter 4, pp. 84-111; Advances in Chemistry. vol. 234; 1994.*
Melde et al. Chem. Mater. vol. 11: 3302-3308; 1999.*
Ichinose et al (1993 Chemistry Letters pp. 1961-1964).*
Lal. et al., Chem. Mater., Sep. 2000, 12(9), pp. 2632-2639.
Synthesis and Characterizations of a Size Series of Highly Luminescent Nanocrystallites; Journal of Physical Chemistry vol. 101, No. 46, Nov. 13, 1997 (pp. 9463-9475).
Ow, Hooisweng, et al., "Fluorescent Silica Nanoparticles for Single Particle Tracking Experiments of Rat Mast Cells", *National Conference: MRS Symposium*, Boston, MA (Nov. 27, 2001).
Ow, Hooisweng, et al., "Silica Based Fluorescent CU-Dots for Single Particle Tracking Experiments", *Poster Session: Nanobiotechnology Center (NBTC)*, (Jun. 25, 2002).
Ow, Hooisweng, et al., "Synthesis and Characterization of Functional Silica Nanoparticles for Labeling, Tracking and Filler Applications", *Poster Session: Cornell Polymer Outreach Program*, (May 20, 2002).

(Continued)

*Primary Examiner* — Christopher M Gross
(74) *Attorney, Agent, or Firm* — Harris Beach PLLC

(57) ABSTRACT

The invention generally relates to fluorescent nanoparticles and more specifically to silica-based fluorescent nanoparticles of less than 30 nm with covalently attached organic dyes. The invention provides a fluorescent monodisperse silica nanoparticle comprising fluorophore center core and a silica shell wherein the radiative properties of the nanoparticle are dependent upon the chemistry (composition) of the core and presence of the silica shell. In one aspect of the invention, the core-shell architecture provides an enhancement in fluorescence quantum efficiency. The invention generally provides control of photophysical properties of dye molecules encapsulated within silica particles with sizes down to 30 nm and below. This control is accomplished through changes in silica chemistry and particle architecture on the nanometer size scale and results in significant brightness enhancement compared to free dye.

15 Claims, 9 Drawing Sheets

OTHER PUBLICATIONS

Stober, Werner, et al., "Controlled Growth of Monodisperse Silica Spheres in the Micron Size Ranger", *Journal of Colloid and Interface Science*, vol. 26, (1968), 26-69.

American Chemical Society, Boston, MA, "Materials Science and Engineering, Chemistry and Chemical Biology", (Aug. 19, 2002).

Srivastava, Mamta, et al., "Single Particle Tracking of Fluorescent Silica Nanoparticles Bound to IgE Receptors on RBL Mast Cells", National Conference: Biophysical Soc. Feb. 2002.

Ow, Hooisweng, et al., "Project Abstract", Poster Session: NYSTAR CAT: Biotechnology. Apr. 23, 2000.

Ow, Hooisweng, et al., Powerpoint Presentation, Poster Session: NYSTAR CAT: Biotechnology. Apr. 23, 2000.

Graft, Christina et al. Dye-Labeled Poly(organosiloxane) Microgels with Core?Shell Architecture Langmuir, 1999, 15 (19), 6170-6180.

Jungmann, Nadja et al. Dye Loading of Amphiphilic Poly(organosiloxane) Nanoparticles. Angewandte Chemie International Edition, Apr. 17, 2003, 142(15), 714-1717.

Xu, Hao et al. A Real-Time Ratiometric Method for the Determination of Molecular Oxygen Inside Living Cells Using Sol?Gel-Based Spherical Optical Nanosensors with Applications to Rat C6 Glioma. Anal. Chem., 2001, 73 (17), 4124-4133.

Blaaderen, A. Van et al. Synthesis and characterization of colloidal dispersions of fluorescent, monodisperse silica spheres.Langmuir, 1992, 8 (12), 2921-2931.

Blaaderen, A. et al. Three-dimensional imaging of submicrometer colloidal particles in concentrated suspensions using confocal scanning laser microscopy. Langmuir, 1992, 8 (6), 1514-1517.

Koo, Yong-Eun Lee et al. Real-Time Measurements of Dissolved Oxygen Inside Live Cells by Organically Modified Silicate Fluorescent Nanosensors. Anal. Chem., 2004, 76 (9), 2498-2505.

Ow, Hooisweng, et al., "Project Abstract", Poster Session: NYSTAR CAT: Biotechnology, (Apr. 23, 2000).

Stober, Werner et al., Controlled Growth of Monodisperse Silica Spheres in the Micron Size Range, Journal of Colloid and Interface Science, vol. 26, (1968) 62-69.

Bruchez, M. et al.,Semiconductor Nanocrystals as Fluorescent Biological Labels, Science, Sep. 25, 1998, 281 (5385), 2013-2016.

Lal, A. et al. Silica Nanobubbles Containing an Organic Dye in a Multilayered Organic/Inorganic Heterostructure with Enhanced Luminescence Chem. Mater. 2000, 12, 2632-2639.

Dabbousi, B.O. et al. (CdSe)ZnS Core-Shell Quantum Dots: Synthesis and Characterization of a Size Series of Highly Luminescent Nanocrystallites. J. Phys. Chem. B 1997, 101, 9463-9475.

* cited by examiner

FLUORESCENT SILICA-BASED NANOPARTICLES

This is a continuation-in-part application based on co-pending non-provisional application U.S. Ser. No. 10/306,614 filed Nov. 26, 2002, the disclosure of which is incorporated by reference.

STATEMENT OF GOVERNMENT RIGHTS

This invention was made with Government support from the National Science Foundation (NSF) under Grant Nos. 9876771 & 0080792 & the National Institutes of Health (NIH) under Grant No. EB001976. The Government has certain rights in the invention.

FIELD OF THE INVENTION

The invention generally relates to fluorescent nanoparticles and more specifically to silica-based fluorescent nanoparticles of less than 30 nm with covalently attached organic dyes.

BACKGROUND OF THE INVENTION

Fluorescent nanoparticles have tremendous promise as indicators and photon sources of biotechnological and information applications such as biological imaging, sensor technology, microarrays, and optical computing. These applications require size-controlled, monodisperse, bright nanoparticles that can be specifically conjugated to biological macromolecules or arranged in higher-order structures.

Two general approaches have emerged in recent years for synthesizing highly fluorescent, water-soluble nanoparticles for use in a range of demanding biological and analytical applications. In the first approach, the nanoparticulate material itself is fluorescent (such as semiconductor nanocrystals or metal nanocrystals). In the second, the fluorescent nanoparticles are based on the incorporation of organic dye molecules. Given the vast diversity of organic dye molecules and the exquisite sensitivity of these dye molecules to their local environment, the latter approach raises the possibility of developing nanoparticles with a broad range of precisely controlled fluorescence characteristics.

Based on the work of Stöber et al., silica nanoparticles with an embedded dye have been synthesized in a range of sizes, colors, and architectures. In all previous reports of photophysical properties, the dye which is covalently bound inside the silica particle is observed to be quenched in comparison to the free dye. However, in the case of poly(organosiloxane) microgels in which the dye is non-covalently attached and loaded through diffusion, a slight increase in fluorescence efficiency is observed. For other materials, for example polystyrene microspheres, the quantum efficiency of the embedded dye is the same or less than the free dye. The quenching of fluorescence is usually attributed to either intraparticle energy transfer or non-radiative decay into the silica matrix. Both of these pathways are likely influenced by the local dye environment within the particle, suggesting that precise control of the architecture within the particle might ameliorate quenching or even lead to fluorescence enhancement.

There is still a need for highly fluorescent nanoparticles less than 30 nm with covalently attached organic dyes.

SUMMARY OF THE INVENTION

The invention relates to a class of silica nanoparticles in which the architecture within the silica particle has marked, controlled effects on the radiative properties of the constituent dye.

The invention provides a fluorescent monodisperse silica nanoparticle comprising fluorophore center core and a silica shell wherein the radiative properties of the nanoparticle are dependent upon the chemistry (composition) of the core and presence of the silica shell. In one aspect of the invention, the core-shell architecture provides an enhancement in fluorescence quantum efficiency. The invention generally provides control of photophysical properties of dye molecules encapsulated within silica particles with sizes down to 30 nm and below. This control is accomplished through changes in silica chemistry and particle architecture on the nanometer size scale and results in significant brightness enhancement compared to free dye.

In another aspect of the invention, the core-shell architecture provides the ability to control the photostability properties of the nanoparticle.

The quantum efficiency increase provided by the invention is due to both an increase in the radiative rate and a decrease in the non-radiative rate, with the latter effect being the most variable between architectures. The changes in non-radiative rate correlate well to differences in rotational mobility of the dye within the particle.

In one embodiment of the invention, the fluorescent monodisperse nanoparticle includes a core-shell architecture wherein the core comprises a compact core surrounded by a silica shell. In another embodiment of the invention, the fluorescent monodisperse nanoparticle includes a core-shell architecture wherein the core comprises an expanded core surrounded by a silica shell. In yet another embodiment of the invention, the fluorescent monodisperse nanoparticle includes a core-shell architecture wherein the core comprises a homogenous particle with dyes sparsely embedded within surrounded by a silica shell. In still another embodiment of the invention, the fluorescent monodisperse homogenous nanoparticle is not surrounded by a silica shell.

The invention provides a method of making a fluorescent monodisperse nanoparticle with a compact core architecture by mixing a fluorescent compound and an organo-silane compound to form a dye precursor, mixing the resulting dye precursor with an aqueous solution to form a compact fluorescent core, and mixing the resulting compact core with a silica precursor to form a silica shell on the compact core, to provide the fluorescent monodisperse nanoparticle.

The invention also provides a method of making a fluorescent monodisperse nanoparticle with an expanded core architecture by mixing a fluorescent compound and an organo-silane compound to form a dye precursor, co-condensing the resulting dye precursor with a silica precursor to form an expanded fluorescent core, and mixing the resulting expanded core with a silica precursor to form a silica shell on the expanded core, to provide the fluorescent monodisperse nanoparticle.

The invention provides a method of making a fluorescent monodisperse homogenous nanoparticle by mixing a fluorescent compound and an organo-silane compound to form a dye precursor and co-condensing the resulting dye precursor with a silica precursor to form a homogenous fluorescent monodisperse nanoparticle.

These and other features of the invention are set forth in the description of the invention which follows.

BRIEF DESCRIPTION OF THE DRAWINGS

FIG. 3 illustrates the steady-state spectroscopy curves showing the quantum efficiency enhancement achieved by the core-shell architecture.

FIG. 4 illustrates the time-resolved fluorescence of nanoparticles.

DETAILED DESCRIPTION OF THE INVENTION

Figure 1A:
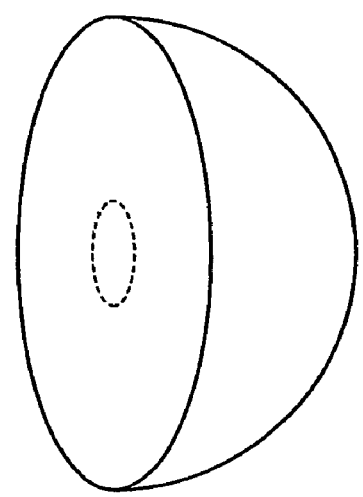
FIG. 1A-C illustrates a schematic of different silica nanoparticle architectures designated as compact core-shell nanoparticle (1A), expanded core-shell nanoparticle (1B), and the homogenous nanoparticle (1C). The silica shell in the compact and expanded core-shell architecture comprises silica without any dye molecules. The homogenous nanoparticle comprises a composite of silica and dye in a matrix.
Figure 1B:
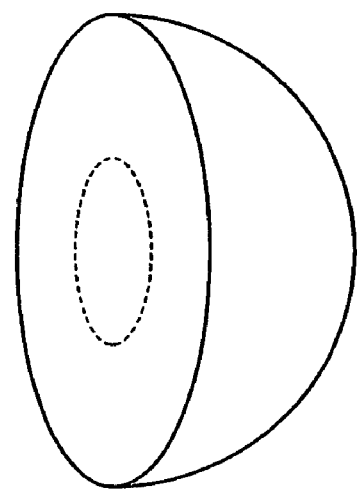
Figure 1C:
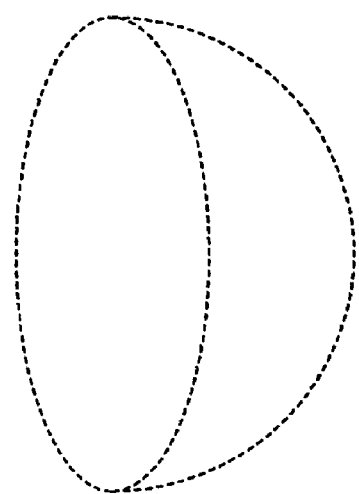

The fluorescent nanoparticles of the present invention include a core comprising a fluorescent silane compound and a silica shell on the core. The core of the nanoparticle can comprise, for example, the reaction product of a reactive fluorescent compound and a co-reactive organo-silane compound, and the shell can comprise, for example, the reaction product of a silica forming compound. The silica forming compound can produce, for example, one or more layers of silica, such as from 1 to about 20 layers, and various desirable shell characteristics, such as shell layer thickness, the ratio of the shell thickness to the core thickness or diameter, silica shell surface coverage of the core, porosity and carrying capacity of the silica shell, and like considerations.

The synthesis of the fluorescent monodisperse core-shell nanoparticles is based on a two-step process. First, the organic dye molecules, tetramethylrhodamine isothiocynate (TRITC), are covalently conjugated to a silica precursor and condensed to form a dye-rich core. Second, the silica gel monomers are added to form a denser silica network around the fluorescent core material, providing shielding from solvent interactions that can be detrimental to photostability. By first forming a dye-rich core enables the incorporation of various classes of fluorophores which cover the entire UV-Vis absorption and emission spectrum.

The amount of reagents used in the synthesis of the different core-shell architectures in terms of dye placement, i.e. compact core, expanded core, and homogenous, have been kept identical to generate precise structure property correlations. However, the order in which the reagents are reacted that resulted in the forming the core-shell architecture varies. Therefore, the chemical environment around the dye molecules in each architecture is different with respect to the silica matrix density and presence of organic moieties which has significant effects on the photophysical particle properties.

For the synthesis of the compact core-shell nanoparticle, the dye precursor was added to a reaction vessel that contains appropriate amounts of ammonia, water and solvent and allowed to react overnight. The dye precursor was synthesized by addition reaction between TRITC and 3-aminopropyltriethoxysilane in molar ratio of 1:50, in exclusion of moisture. After the synthesis of the dye-rich compact core was completed, tetraethylorthosilicate (TEOS) was subsequently added to grow the silica shell that surrounded the core.

The synthesis of the expanded core-shell nanoparticle was accomplished by co-condensing TEOS with the aforementioned dye precursor and allow the mixture to react overnight. After the synthesis of the expanded core was completed, additional TEOS was added to grow the silica shell that surrounded the core.

The synthesis of the homogenous nanoparticles was accomplished by co-condensing all the reagents, the dye precursor and TEOS, at the same time and allow the mixture to react overnight.

Figure 2A:
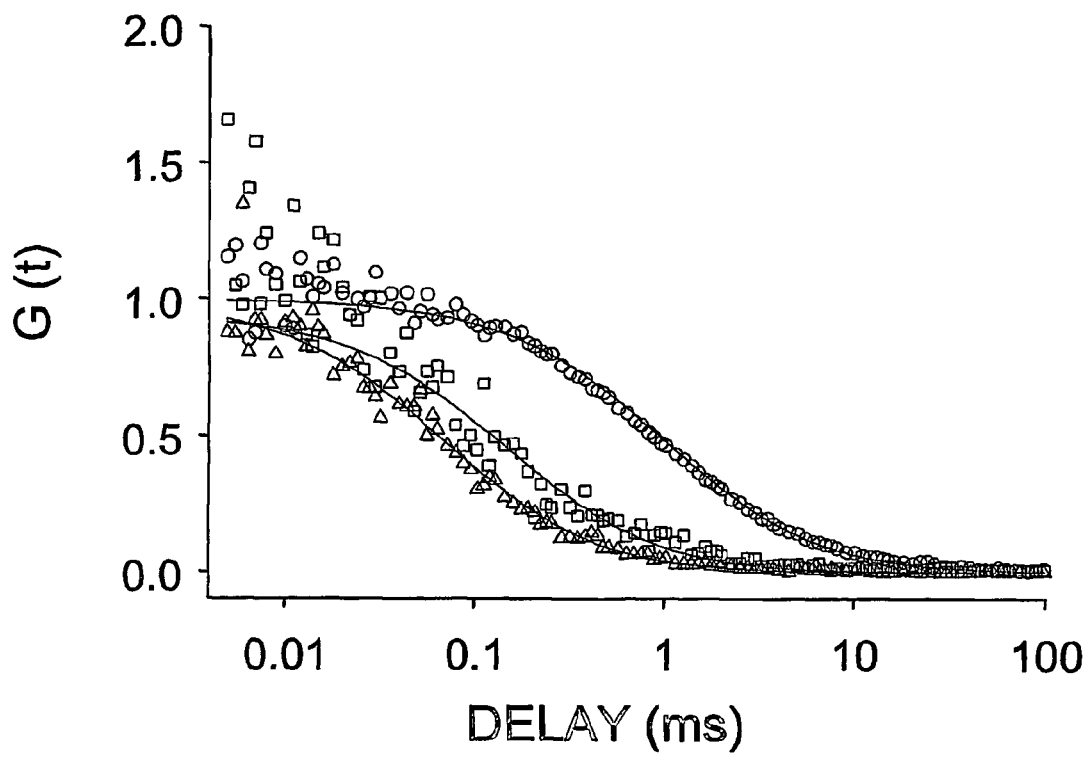
FIG. 2A-C illustrates fluorescence correlation spectroscopy of nanoparticles and synthetic intermediates.
Figure 2B:
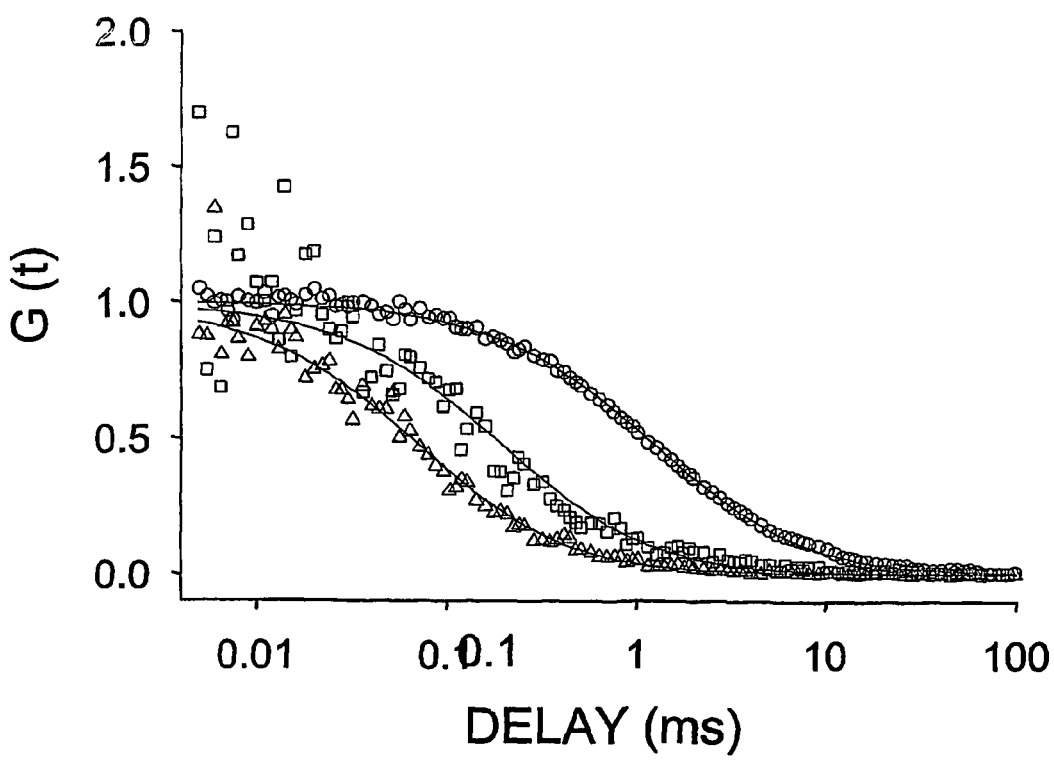
Figure 2C:
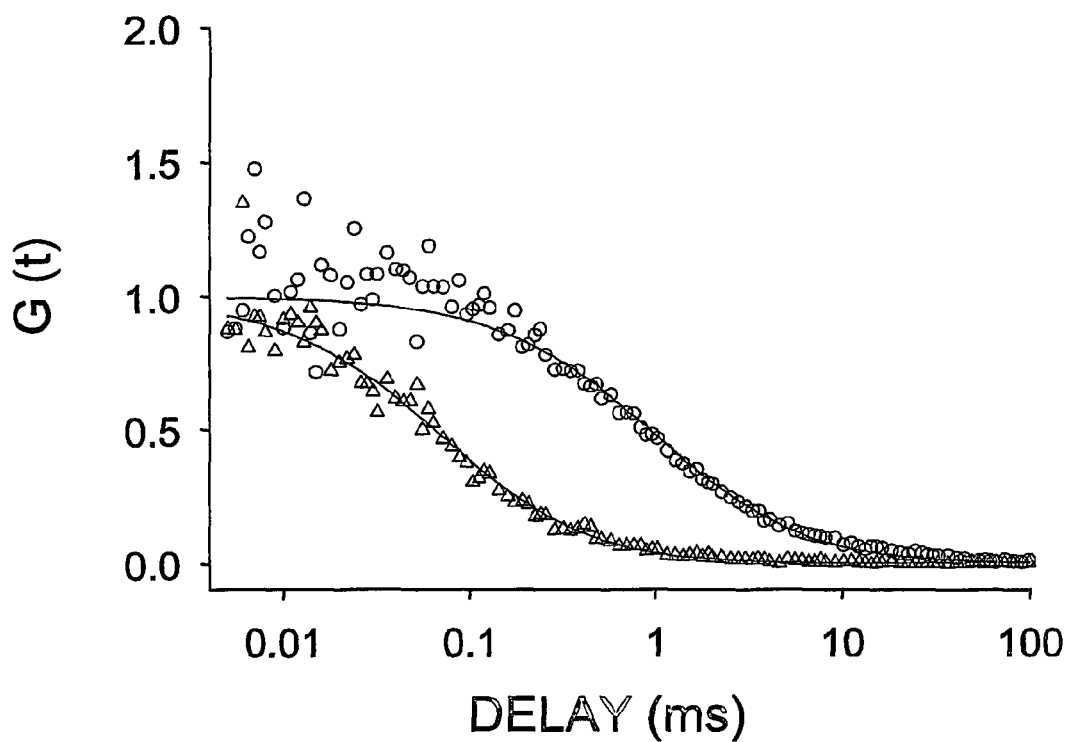

The FCS curves and monoexponential fits shown in FIG. 2A-C illustrate the monodispersity requirement for each architecture in an aqueous solution. The FCS curve further provides two independent parameters: the diffusion coefficient and the absolute concentration. The diffusion coefficient is directly related to the hydrodynamic radius, and the absolute concentration allows quantification of the particle brightness.

FCS curves for each nanoparticle and its respective intermediate are shown in FIG. 2A-C. As shown in FIG. 2A, the diffusion coefficient of the core (D=0.098 $\mu m^2$/ms) for the compact core-shell architecture, is about half that of free TRITC dye (D=0.21 $\mu m^2$/ms). The complete nanoparticle is about ten times bigger, as shown in FIG. 2A (D=0.014 $\mu m^2$/ms). A similar relationship between the free TRITC dye, expanded core-shell architecture and complete nanoparticle is shown in FIG. 2B. The diffusion coefficient of the core in the expanded core-shell architecture is 0.075 $\mu m^2$/ms compared to a diffusion coefficient value of the free dye TRITC (D=0.21 $\mu m^2$/ms). For the homogenous nanoparticle, there is no intermediate core structure, so FIG. 2C illustrates the diffusion coefficient of the homogenous nanoparticle (D=0.015 $\mu m^2$/ms) relative to the free TRITC dye.

Figure 2D:
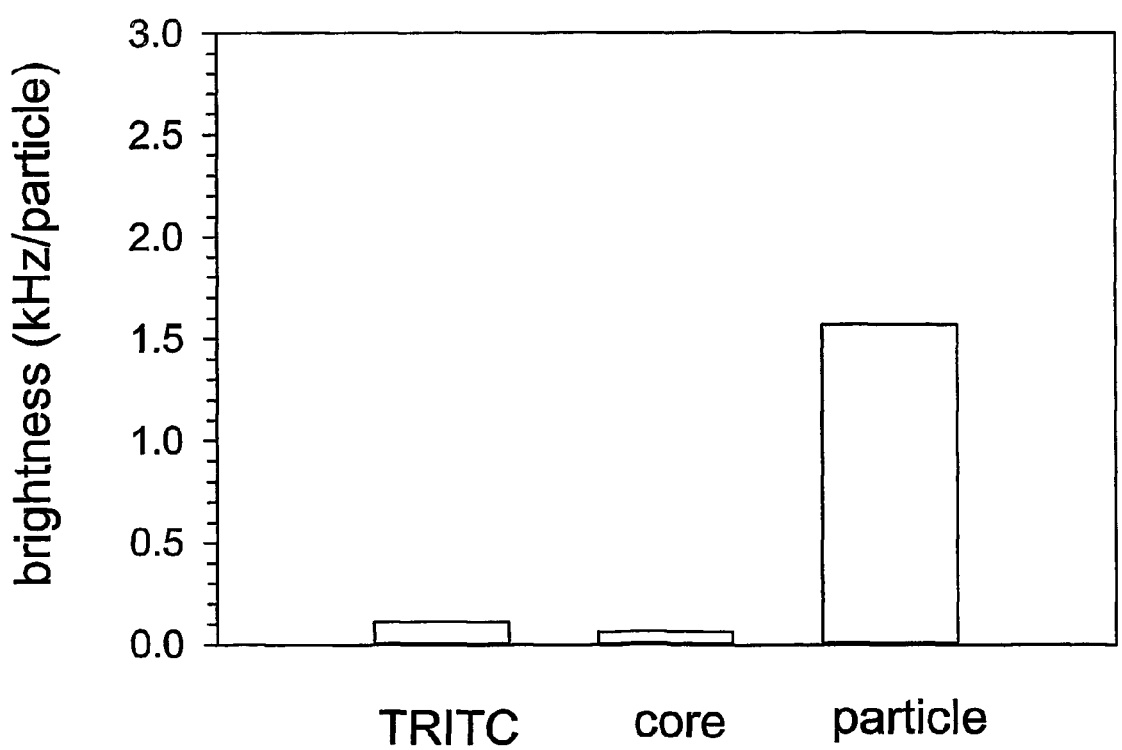
FIG. 2D-F illustrates the brightness (counts/particles/second) values for the synthesis stages of the compact core-shell architecture, expanded core-shell architecture and the homogenous architecture based on excitation value of 1.2 mW at 900 nm.
Figure 2E:
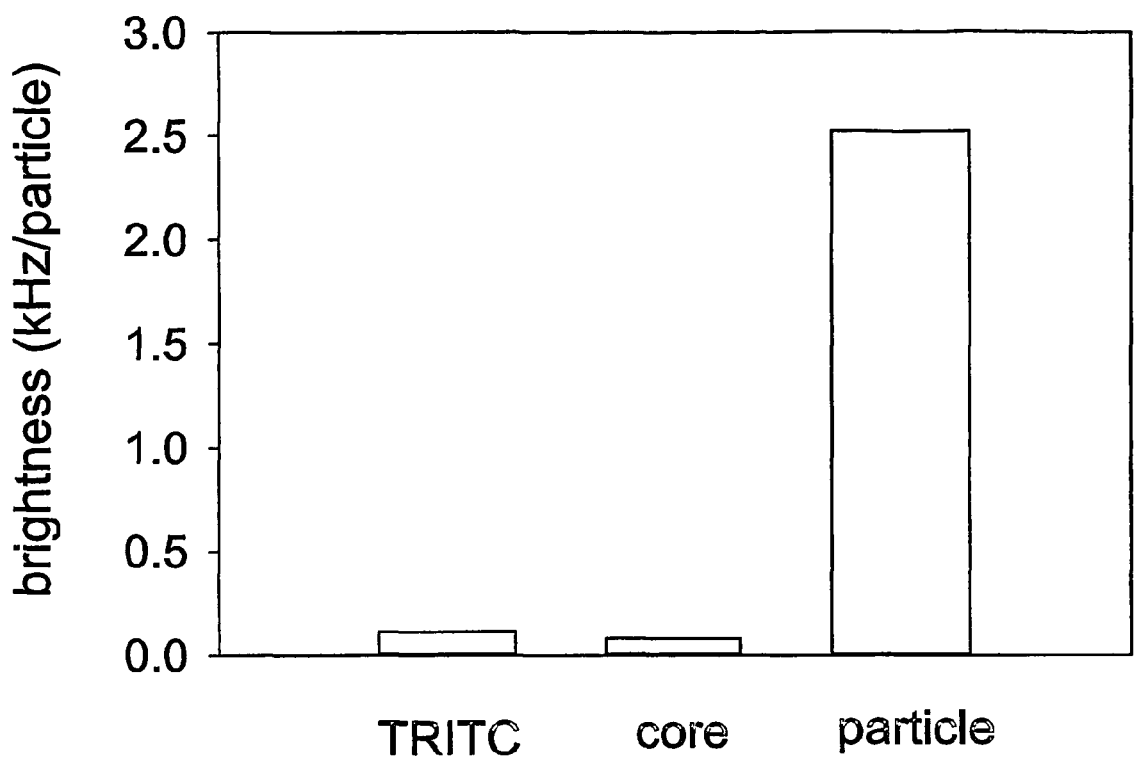
Figure 2F:
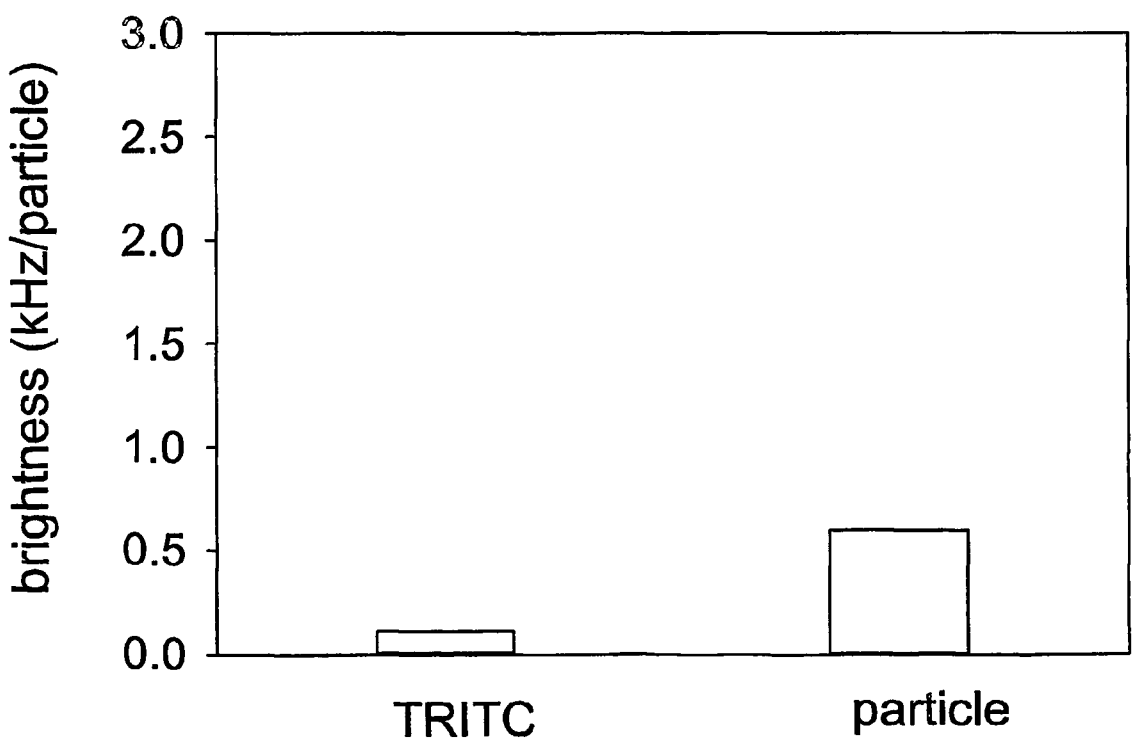

FIG. 2D-E illustrates the brightness of each architecture and synthesis intermediates. For the syntheses which proceed with a core intermediate, the core is always dimmer than the free dye, despite the fact that multiple dyes are presumably present in the core. The brightness of the complete nanoparticle is always significantly greater than free dye and/or core intermediate. Furthermore, the brightness varies for the different architectures despite their same particle size and same absolute amounts of precursor materials.

The fluorescent nanoparticles of the invention include an organic dye, TRITC, which demonstrates quantum efficiency enhancement effects in its luminescent properties. When the fluorescent nanoparticles of the invention are illuminated with a primary energy source, a secondary emission of energy occurs at a frequency corresponding to band gap of the organic dye used in the nanoparticle.

Figure 3A:
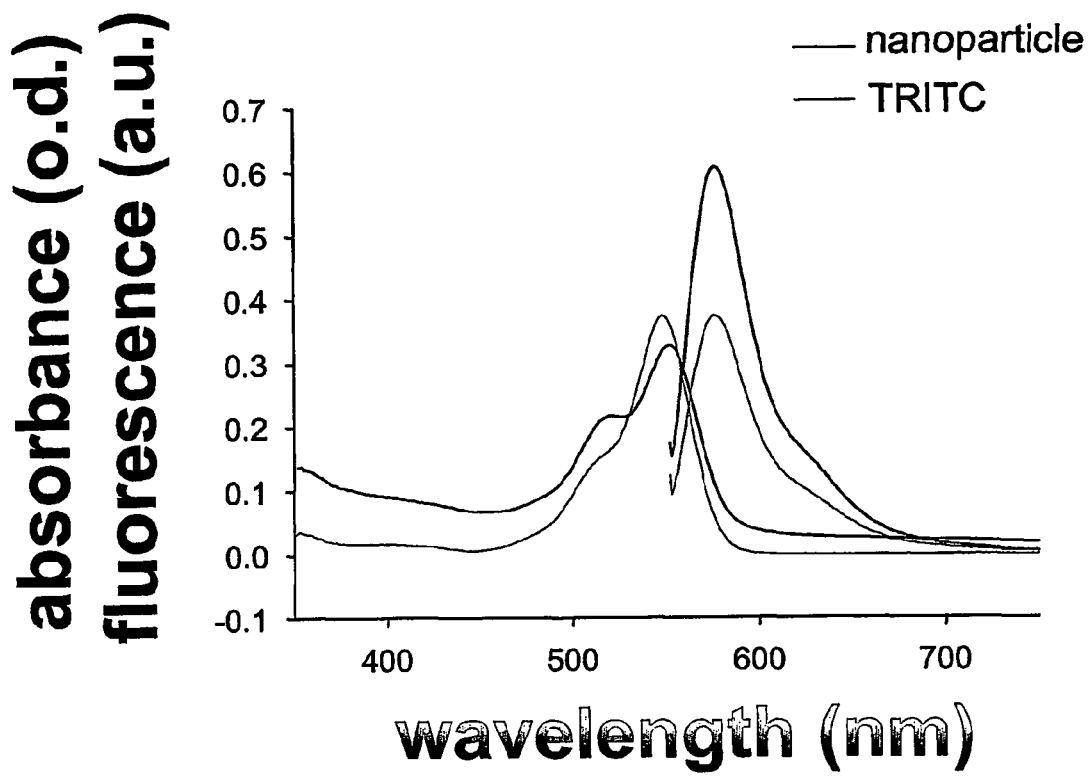
FIGS. 3A-C illustrate the absorbance and fluorescence of the compact core-shell nanoparticle (3A), expanded core-shell nanoparticle (3B) and homogenous nanoparticle (3C). The absorbance values are in units of optical density. The fluorescence is scaled relative to the organic dye used, TRITC.
Figure 3B:
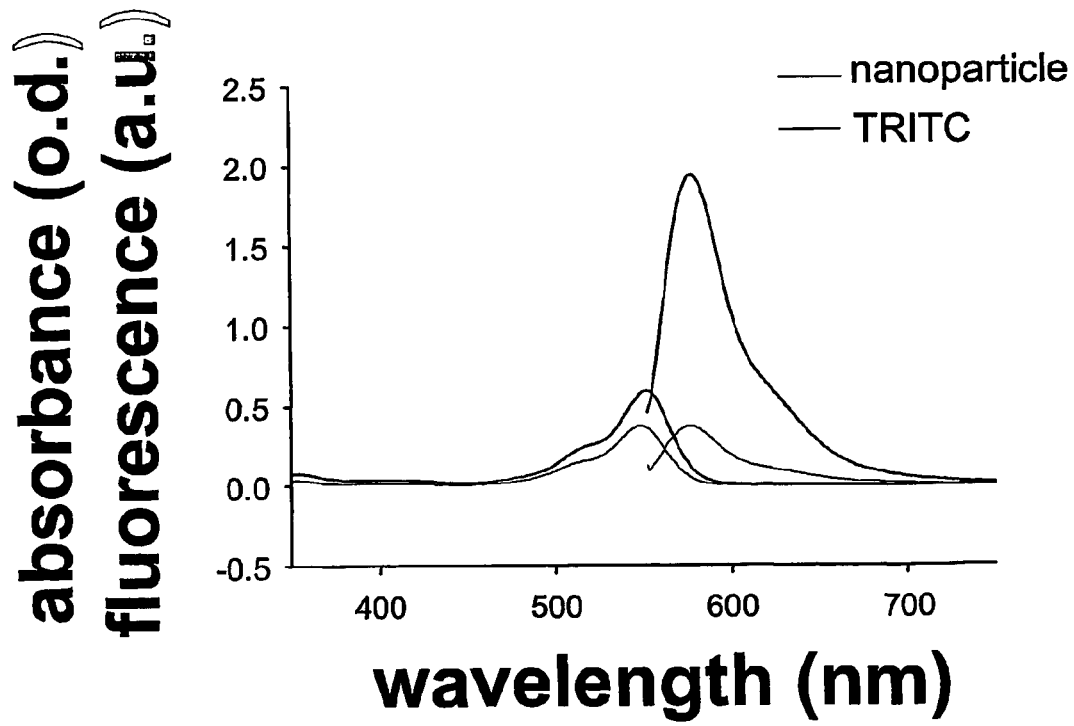
Figure 3C:
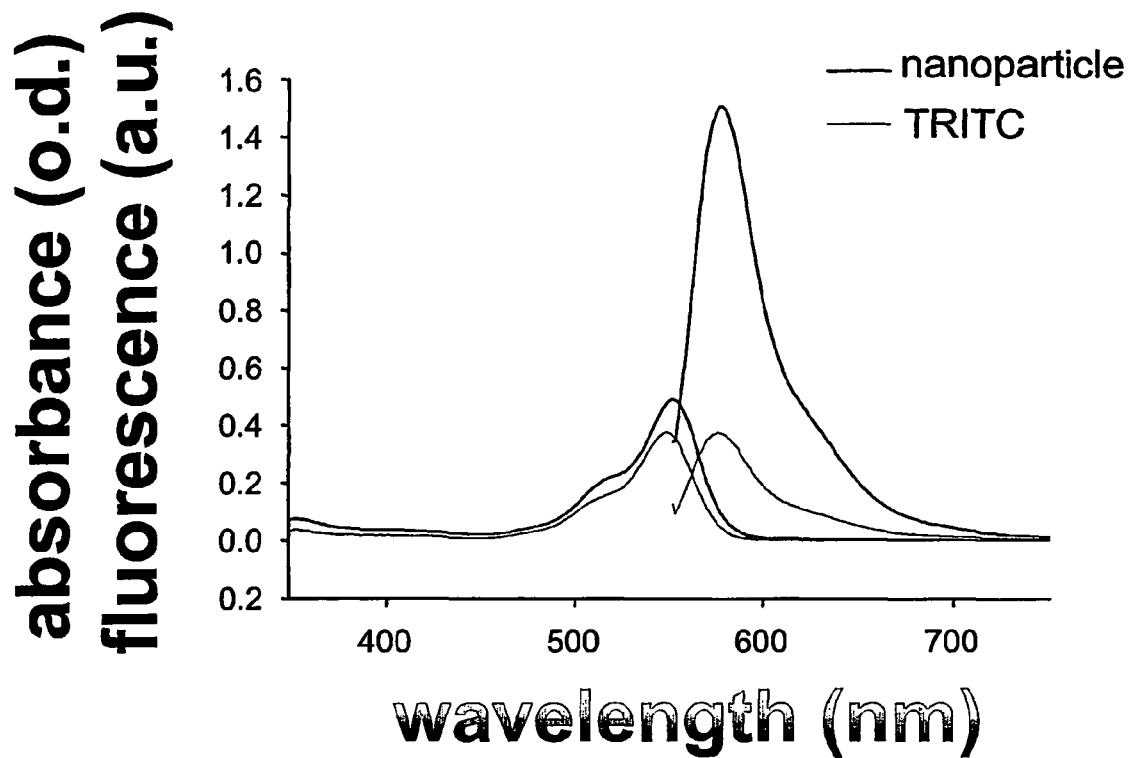
Figure 3D:
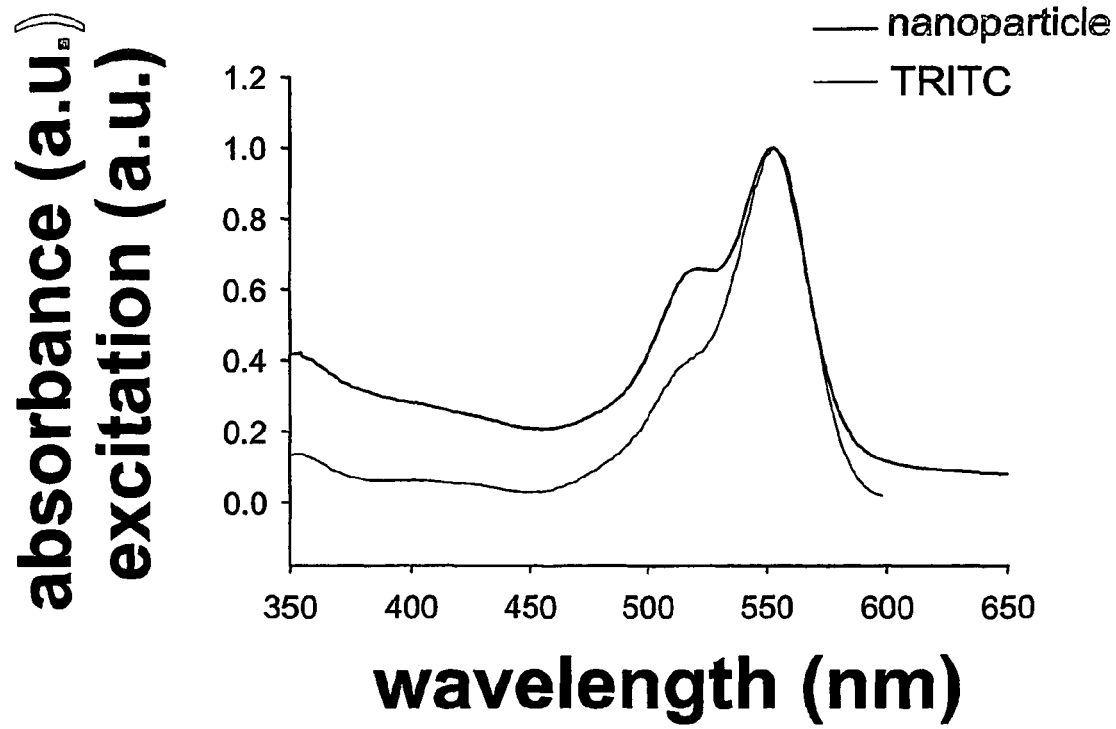
FIGS. 3D-F illustrate the comparison between absorbance and excitation for the compact core-shell nanoparticle (3D), expanded core-shell nanoparticle (3E), and homogenous particle (3F).
Figure 3E:
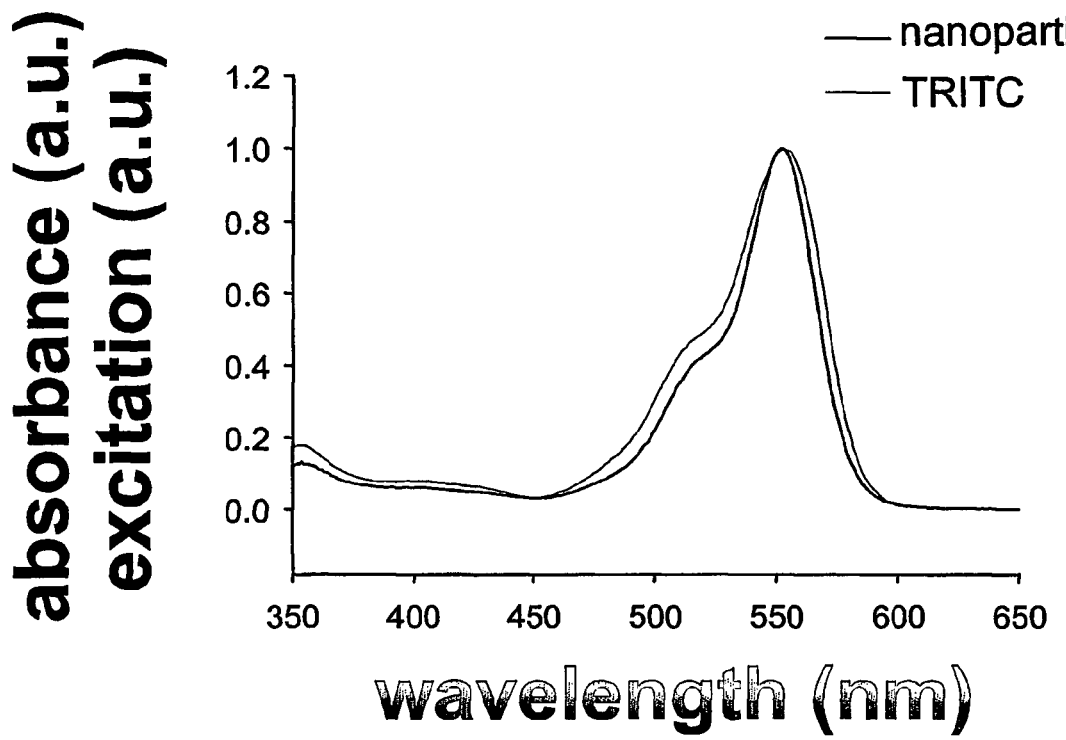
Figure 3F:
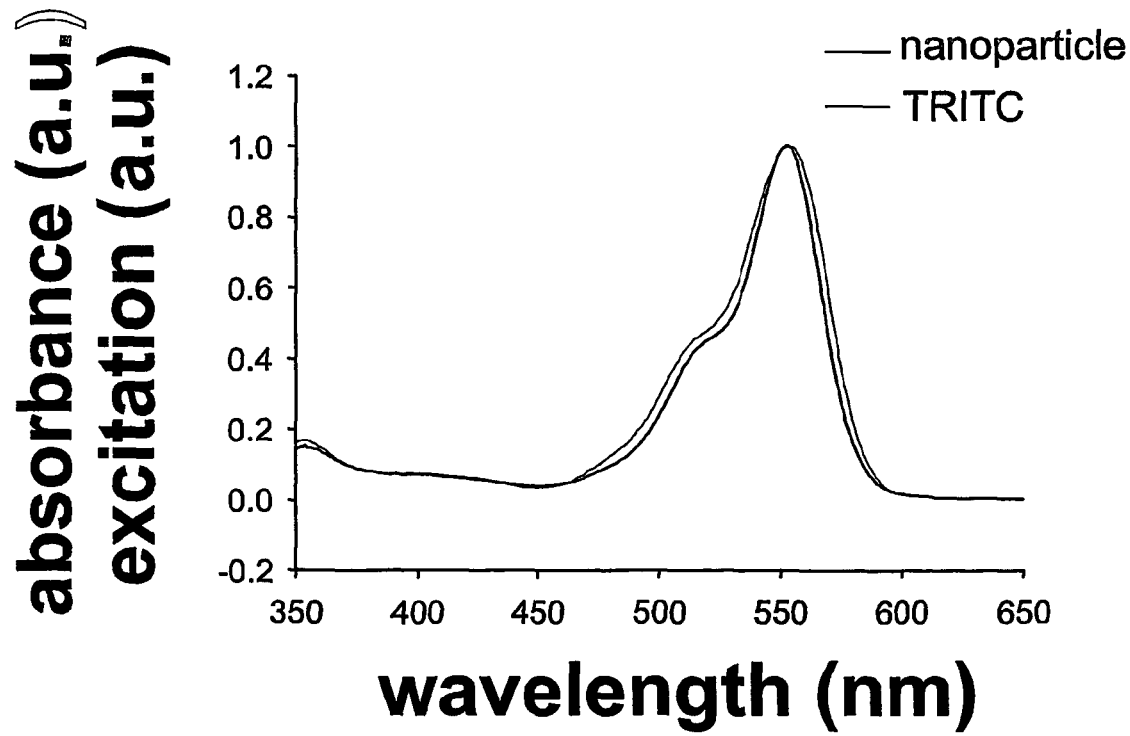

The number of TRITC equivalents per particle can be determined through a combination of FCS and absorbance measurements, in which the absolute concentration is determined from FCS and the relative absorbance is measured with respect to TRITC in solution, as shown in FIG. 3A-C. Dilute solutions were used (about 50 nM) in FIG. 3A-C so that a sample could be measured by both FCS and absorbance. The number of TRITC equivalents per particle, calculated using an extinction coefficient of 42,105 M$^{-1}$ cm$^{-1}$ at 514.5 nm are shown in Table II. Similarly, the relative intensities of the nanoparticle fluorescence and nanoparticle absorbance give the quantum efficiency enhancement over free TRITC, as shown in Table II.

For the compact core-shell and expanded core-shell nanoparticles, the number of TRITC equivalents per particle is indistinguishable at 8.6. However, the expanded core-shell nanoparticle shows a three-fold quantum efficiency enhancement compared to the free TRITC dye, while the compact core-shell exhibits only a two-fold quantum efficiency enhancement compared to the free TRITC dye, as shown in FIGS. 3A, B and Table II. The largest quantum efficiency enhancement was observed with the homogenous nanoparticle, which has on average 2.3 TRITC equivalents per particle, as shown in FIG. 3C and Table II.

The ability to control the photophysical properties through the nanoparticle chemistry and architecture enables both the development of the next generation fluorescent probes and the study of fluorescent properties that might be inaccessible in solution.

Figure 4A:
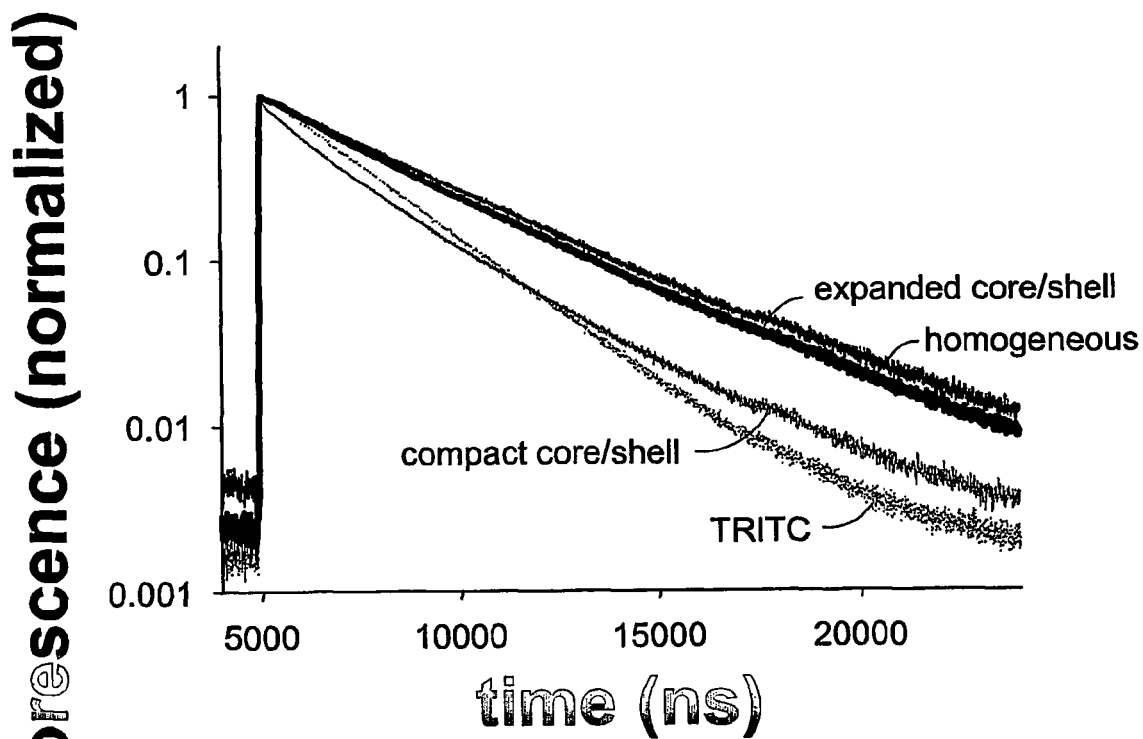
FIG. 4A illustrates the normalized fluorescence decay of a homogenous nanoparticle, expanded core-shell nanoparticle, compact core-shell nanoparticle and the TRITC dye.

The fluorescence lifetime of the particles is shown in FIG. 4A. Each lifetime, including free TRITC, is multiexponential and the average lifetime values are compiled in Table III. The lifetime of TRITC ($\tau_f$=2.1 ns) is in good agreement with the literature value in water. The lifetime increases from the compact core-shell (1.8 ns) to the expanded core-shell (2.9 ns) to the homogeneous particle (3.2 ns) (FIG. 4A). The compact-core shell has a lifetime which is less than free dye, although the dominant contribution to this lifetime is a fast component (FIG. 4A). From this lifetime data alone, one might conclude that the dye is quenched inside the compact core-shell particle, but the steady state measurements suggest otherwise. The combination of fluorescence lifetime and quantum efficiency allow for a unique determination of the radiative and non-radiative rate constants, tabulated in both normalized and absolute form in Table III. The enhancement of the radiative rate is constant across the different architectures and is 2.2 fold greater than free TRITC. However, the non-radiative rate varies across architectures from a relatively high value for the compact core-shell nanoparticles to a value almost 3 fold less for the homogeneous particles.

Figure 4B:
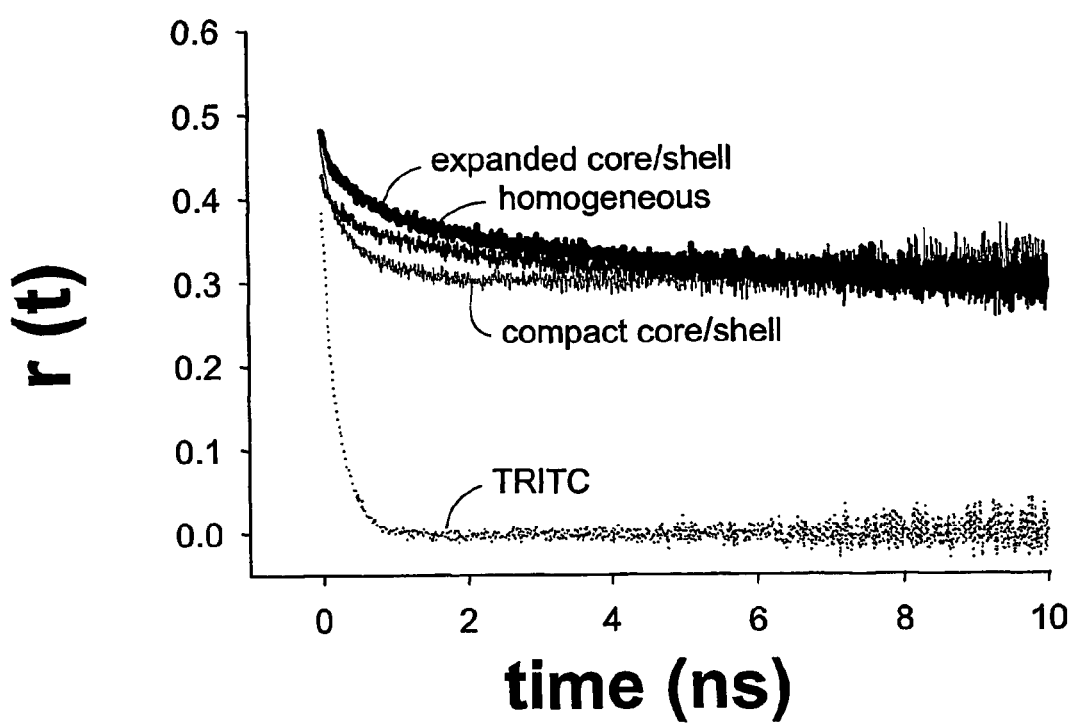
FIG. 4B illustrates the fluorescence anisotropy of an expanded core-shell nanoparticle, a compact core-shell nanoparticle, a homogenous nanoparticle, and the TRITC dye.

The rotational anisotropy of the particles again shows complicated, multiexponential behavior (FIGS. 4B, C), and we restrict ourselves at present to the average rotational time constant (Table III, θ). As expected, the rotation of the dye inside the particle is hampered by the silica matrix, leading to longer rotation times than free dye (FIG. 4B). In fact, the anisotropy curves do not decay to zero on the timescale of the measurement, in contrast to the coumarin control (note that there is also some residual anisotropy of free TRITC). However, there is still a remarkable degree of rotational mobility, even inside the tightly packed core of the nanoparticle. The time scales of rotation are too fast to be overall rotation of the entire 30 nm nanoparticle and too slow to be depolarization due to energy transfer. Furthermore, the amplitude of the curve (r(0)) is near the theoretical amplitude for two-photon anisotropy (r(0)=0.57), suggesting that there is not the fast depolarization usually associated with energy transfer.

Figure 4C:
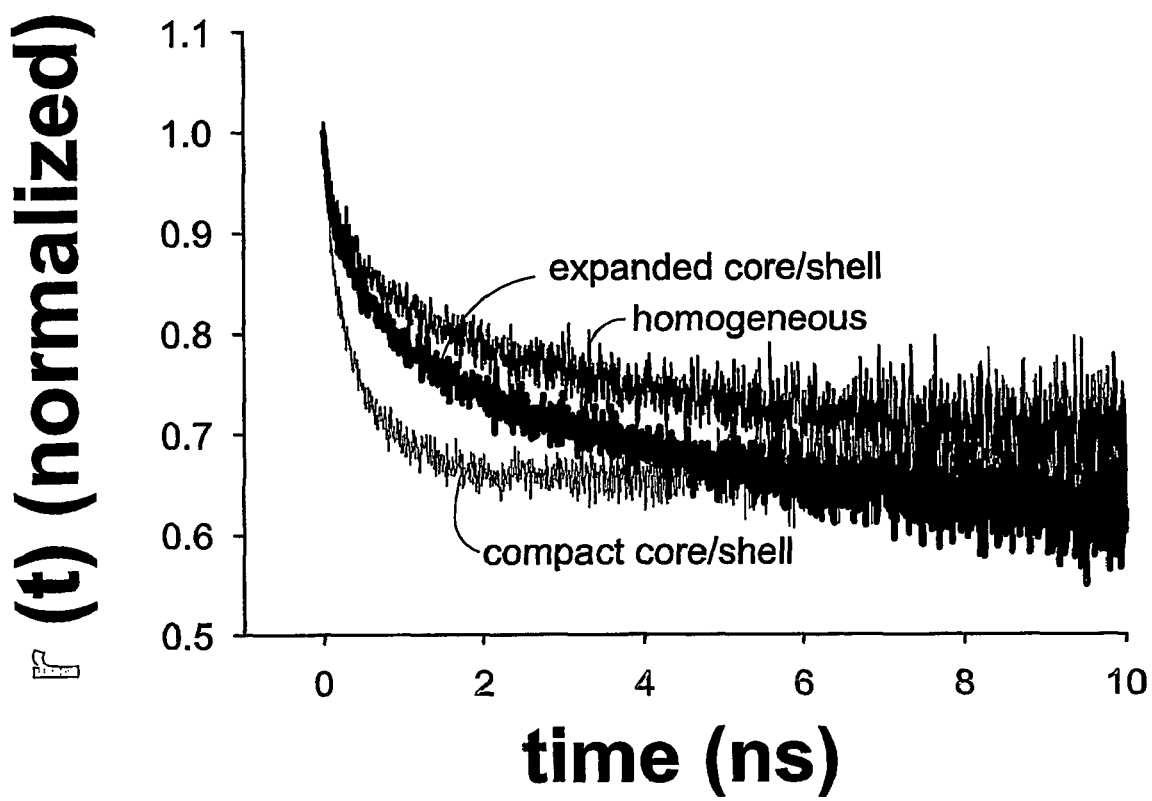
FIG. 4C illustrates the normalized fluorescence anisotropy of the nanoparticle curves shown in FIG. 4B. Average fit values for the fluorescence lifetime ($\tau_f$) and rotational lifetime ($\theta$) are compiled in Table III.

It is therefore likely that the decay in anisotropy is due to hindered rotation of the dye molecules within the silica matrix. The scaled anisotropy for each architecture is shown in FIG. 4C. The compact core-shell nanoparticle has the fastest, least hindered rotation (FIG. 4C), followed by the expanded core-shell particle (FIG. 4C), and finally the homogeneous nanoparticle (FIG. 4C). This rotation time has a monotonic, inverse dependence on the non-radiative rate constant (Table III), suggesting that the confined mobility in the silica nanoparticle is responsible for suppression of non-radiative decay.

Nanoparticle Synthesis Materials

Absolute ethanol (Aldrich), Tetrahydrofuran (Aldrich), Ammonium hydroxide (Fluka, 28%), Tetraethoxysilane (Aldrich, 98%), 3-Aminopropyltriethoxysilane (Aldrich, 99%), 3-Mercaptopropyltriethoxysilane (Gelest, 99%), Tetramethylrhodamine-5-(and -6-)-isothiocyanate*mixed isomers* (TRITC) (Molecular Probes, 88%), Alexa Fluor® 488 C$_5$ Meleimide (Molecular Probes, 97%), Alexa Flour® 488 carboxylic acid, and succinimidyl ester (Molecular Probes, ≧50%).

Preparation of Core (Fluorescent Seed) Nanoparticles Generally

Amounts of water, ammonia and solvent were measured in graduated cylinders. Fluorescent seed particle synthesis was carried out in 1 L Erlenmeyer flasks and stirred with magnetic TEFLON® coated stir bars at about 600 rpm. De-ionized water and ammonia solution were added to ethanol and stirred. About 2 nL of the reactive dye precursor in either ethanol or THF containing about 425 micromolar APTS, was added to the reaction vessel. Depending on the desired architecture, the resulting mixture was stirred from 1 to 12 hours at room temperature with the reaction vessel covered with aluminum foil to minimize exposure to light to afford a fluorescent seed particle mixture. Tetrahydrofuran (THF) and absolute ethanol (EtOH) were distilled under nitrogen. Organic dyes were brought to room temperature from storage temperatures of about −20° C., and then placed in a glove box.

Preparation of the Silica Shell on the Core (Fluorescent Seed) Particles Generally The silica shell coating and growth step was performed in the above mentioned fluorescent seed particle reaction mixture with regular addition of solvent, such as ethanol, methanol, or isopropanol, to prevent drastic changes in solution ionic strength while the silica forming monomer tetraethoxysilane (TEOS) was added. This prevents particle aggregation during synthesis, which can broaden the particle size distribution.

Characterization of Fluorescence Nano-Particles

The particle size and particle size distribution of the resulting fluorescent nanoparticles were characterized by electron microscopy (SEM) and fluorescence correlation spectroscopy (FCS).

Fluorescence Correlation Spectroscopy—All FCS measurements were done on a custom FCS microscope based on two-photon excitation. The instrument consists of a Ti:sapphire oscillator with ~100 fs pulsewidth and 80 MHz rep. rate pumped by an Ar+ ion laser (Spectra Physics, Palo Alto, Calif.). The beam was positioned with a Bio-Rad MRC 600 confocal scan box (Hercules, Calif.) coupled to a Zeiss Axiovert 35 inverted microscope. Excitation light was focused with Zeiss 63x C-Apochromat water immersion objective (N.A.=1.2), and emission was collected through the same objective. The fluorescence was separated from the excitation with a 670 DCLP dichroic and passed through a HQ575/150 emission filter to a GaAsP photon-counting PMT. The resulting photocurrent was digitally autocorrelated with an ALV 6010 multiple tau autocorrelator.

The autocorrelation function $G(\tau)$ is defined as:

$$G(\tau) = \frac{<\partial F(0)\partial F(\tau)>}{<F(\tau)>^2} \quad (1)$$

where $F(\tau)$ is the fluorescence obtained from the volume at delay time $\tau$, brackets denote ensemble averages, and $\delta F(\tau) = F(\tau) - <F(\tau)>$. The fitting function is the standard function for one-component, three-dimensional diffusion:

$$G(\tau) = \frac{1}{N}\left(1 + \frac{4D\tau}{w_{xy}^2}\right)^{-1}\left(1 + \frac{4D\tau}{w_z^2}\right)^{-1/2} \quad (2)$$

where $w_{xy}$ and $w_z$ are the lateral and axial dimensions of the two-photon focal volume, respectively; N is the number of diffusing species in the focal volume; D is the diffusion coefficient. All FCS measurements were carried out with an excitation wavelength of 900 nm. At this wavelength, the lateral dimension was determined to be 0.248 micro meters and the axial dimension was determined to be 0.640 micro meters. The concentration calibration was determined from standard samples of rhodamine green to be 1.43 nM/particle (i.e. N=1 corresponds to 1.43 nM).

Photobleaching—For photobleaching experiments, 30 μL of sample was illuminated continuously in a 3 mm pathlength quartz cuvette (Starna). The excitation was the 514 nm laser line from an argon laser with a power of 5 W and a spot size of 1.5 cm. The samples were prepared with similar absorbance at the excitation wavelength of 514 nm.

Fluorescence is collected at right angle to the excitation through an HQ605/90 emission filter and recorded with a bialkali PMT (HCC125-02, Hamamatsu).

The following examples are presented for the purposes of illustration only and are not limiting the invention.

Example 1

TABLE I

Hydrodynamic radii of nanoparticles and nanoparticle cores.

| Nanoparticle | Core radius (nm) (SD) | Core/shell radius (nm) (SD) |
|---|---|---|
| Compact core/shell | 2.2 (0.3) | 15 (1.2) |
| Expanded core/shell | 2.9 (0.3) | 17 (1.4) |
| Homogeneous | — | 15 (1.1) |

The hydrodynamic radii calculated at 21° C. are tabulated in Table I. Each nanoparticle curve fits with a single diffusion coefficient and the hydrodynamic sizes are equal within the error of the measurement (r=15, 17 nm). For the core intermediates, the expanded core is slightly larger (r=2.9 nm) than the compact core (r=2.2 nm).

Example 2

TABLE II

Brightness of nanoparticles

| Sample | TRITC equivalents | QE enhancement | Brightness factor | Counts/ particle |
|---|---|---|---|---|
| TRITC | 1.0 | 1.0 | 1.0 | 1.0 |
| Compact core/shell | 8.6 | 2.0 | 18. | 14. |
| Expanded core/shell | 8.7 | 3.1 | 27. | 22. |
| Homogeneous | 2.3 | 3.3 | 7.5 | 6.0 |

The amplitude of the autocorrelation provides the number of the diffusing species and the average count rate is a measure of the photons collected from the optically defined focal volume. From this data, the count rate per molecule for each diffusing species can be obtained, which is a direct measure of the brightness of a probe.

The overall enhancement of brightness of the particle over free dye is the product of the number of TRITC equivalents inside the nanoparticle and the relative quantum efficiency enhancement of the dye, as shown in Table II, brightness factor. However, given the uncertainty in the determination of TRITC equivalents, it is necessary to have an additional, independent measure of brightness for comparison, such as the counts per particle measured from FCS (Table II, counts/particle). The brightness factor is similar to the independent brightness determination from FCS (Table II, comparing last two columns), and the trend for brightness over the different architectures is the same by both methods. The brightness factor consistently overestimates the values measured by FCS, possibly due to the error in the determination of dye equivalents.

The enhancement of the quantum efficiency can be due, in general, to an increase in the radiative rate ($k_r$), a decrease in the non-radiative rate ($k_{nr}$), or both. The relative contributions of these factors are related to the fluorescence lifetime ($\tau_f$) and the quantum efficiency ($\phi$) by:

$$\tau_f = \frac{1}{k_r + k_{nr}} \quad (1)$$

$$\phi = \frac{k_r}{k_r + k_{nr}} \quad (2)$$

Example 3

TABLE III

Time-resolved parameters for silica nanoparticles

| Sample | <lifetime> ns | $\phi$ | $k_r$ ns$^{-1}$ | $k_r$ (normalized) | $k_{nr}$ ns$^{-1}$ | $k_{nr}$ (normalized) | <θ> ns |
|---|---|---|---|---|---|---|---|
| TRITC | 2.1 | 0.15 | 0.072 | 1.0 | 0.41 | 1.0 | 0.21 |
| Compact core-shell | 1.8 | 0.30 | 0.17 | 2.3 | 0.39 | 0.95 | 0.40 |
| Expanded core-shell | 2.9 | 0.47 | 0.16 | 2.2 | 0.18 | 0.45 | 3.2 |
| Homogeneous | 3.2 | 0.50 | 0.16 | 2.2 | 0.16 | 0.39 | 6.7 |

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A fluorescent silica-based nanoparticle comprising:
   (a) a silica-based core comprising:
     an organic functional group wherein the organic functional group comprises a mercapto substituent, and
     an organic fluorescent compound throughout the silica-based core; and
   (b) a silica shell surrounding at least a portion of the core, wherein the fluorescent silica-based nanoparticle has a diameter of 70 nm or less and is conjugated to a ligand.

2. The fluorescent silica-based nanoparticle of claim 1, wherein the diameter is 50 nm or less.

3. The fluorescent silica-based nanoparticle of claim 1, wherein the ligand comprises at least one of a protein.

4. The fluorescent silica-based nanoparticle of claim 1, wherein the ligand is conjugated to the nanoparticle by a linkage, wherein the linkage is an ester, an amide, a thioester or a sulfate ester linkage.

5. The fluorescent silica-based nanoparticle of claim 1, wherein the silica shell covers from about 10 percent to about 100 percent of the surface area of the core.

6. The fluorescent silica-based nanoparticle of claim 1, wherein the silica-based core further comprises a silica-based network, wherein the fluorescent compound is covalently attached to the silica-based network.

7. The fluorescent silica-based nanoparticle of claim 1, wherein the fluorescent quantum yield of the fluorescent organic dye in the nanoparticle is about two-fold to about three-fold greater than the fluorescent quantum yield of the same fluorescent organic dye free in aqueous solution.

8. The fluorescent silica-based nanoparticle of claim 1, the mercapto substituent is bonded to a maleimide.

9. The fluorescent silica-based nanoparticle of claim 1, wherein the silica-based core has a radius between about 1.6 nm and about 3.5 nm.

10. The fluorescent silica-based nanoparticle of claim 1, wherein the silica-based core has a radius between about 2.2 nm and about 2.9 nm.

11. The fluorescent silica-based nanoparticle of claim 1, comprising a therapeutic agent, wherein the therapeutic agent is associated with the ligand.

12. The fluorescent silica-based nanoparticle of claim 1, wherein the ligand comprises at least one of a polypeptide.

13. The fluorescent silica-based nanoparticle of claim 1, wherein the ligand comprises at least one of a biopolymer.

14. The fluorescent silica-based nanoparticle of claim 1, wherein the ligand comprises at least one of a synthetic polymer.

15. The fluorescent silica-based nanoparticle of claim 1, wherein the ligand comprises at least one of an oligopeptide.

* * * * *